(12) United States Patent
Kim et al.

(10) Patent No.: US 6,284,912 B1
(45) Date of Patent: Sep. 4, 2001

(54) PROCESS FOR SYNTHESIZING PARA-AND/OR META-SUBSTITUTED CYANOPHENYALANINE DERIVATIVES

(75) Inventors: Bong Chan Kim; Sang Yeul Hwang; Jong Chan Lim; Do Hyun Nam; Hyun Ik Shin, all of Taejon (KR)

(73) Assignee: LG Chemical, Ltd., Seoul (KR)

( * ) Notice: Subject to any disclaimer, the term of this patent is extended or adjusted under 35 U.S.C. 154(b) by 0 days.

(21) Appl. No.: 09/540,597

(22) Filed: Mar. 31, 2000

(30) Foreign Application Priority Data

Apr. 9, 1999 (KR) .................................. 99-12513

(51) Int. Cl.$^7$ .................................. C07C 255/00
(52) U.S. Cl. .................................. 558/414
(58) Field of Search .................. 558/414; 546/230; 548/569

(56) References Cited

PUBLICATIONS

Jendralla et al., "Efficient Kg–Scale Synthesis of Thrombin Inhibitor CRC 220", Tetrahedron, vol. 51, No. 44, pp. 12047–12068, 1995.
Pearson et al., "Thrombus Imaging Using Technetium–99m–Labeled High–Potency GPIIb/IIIa Receptor Antagonists. Chemistry and Initial Biological Studies", J. Med. Chem., vol. 39, pp. 1372–1382, 1996.
Vadon et al., "Synthesis and effects on arginase and nitric oxide synthase of two novel analogues of N–hydroxyarginine, N–hydroxyindospicine and p–hydroxyamidinophenylalanine", J. Chem. Soc., Perkin Trans. 1, pp. 645–648, 1996.
Myers et al., "Highly Practical Methodology for the Synthesis of D—and L–α–Amino Acids, N–Protected α–Amino Acids and N–Methyl–α–amino Acids", J. Am. Chem. Soc. vol. 119; 1997.
Takagi et al., Chemistry Letters, pp. 1957–1958, 1989.
Kubota et al., "Palladium–Catalyzed Cyanation of Hindered, Electron–Rich Aryl Triflates by Zinc Cyanide", Tetrahedron Letters, vol. 39, pp. 2906–2910, 1998.
Sakakibara et al., "The Cyanation of Aromatic Halides Catalyzed by Nickel (0) Complexes Generated in situ. I. General Scope and Limitations", Bull. Chem. Soc. Jpn., Vol. 61, pp. 1985–1990, 1988.
Takagi et al., "Nucleophilic Displacement Catalyzed by Transition Metal. IX", Bull. Chem. Soc. Jpn., 64, pp. 1118–1121, 1991.

*Primary Examiner*—Joseph K. McKane
*Assistant Examiner*—Joseph Murray
(74) *Attorney, Agent, or Firm*—Peter F. Corless; Christine O'Day; Dike, Bronstein, Roberts and Cushman, Intellectual Property Practice Group

(57) ABSTRACT

The present invention relates to a process for preparing a useful medicinal intermediate represented by the following formula (1):

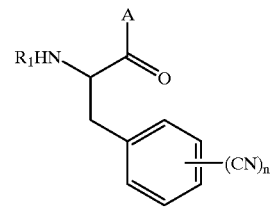

in which, $R_1$, A and n are defined as described in the specification, or its stereoisomer, characterized in that a compound represented by the following formula (2):

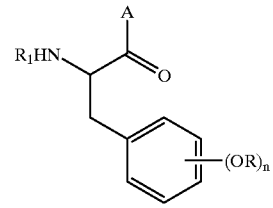

in which, R, $R_1$, A and n are defined as described in the specification, is reacted with a cyanide in the presence of a nickel catalyst.

17 Claims, No Drawings

PROCESS FOR SYNTHESIZING PARA-AND/OR META-SUBSTITUTED CYANOPHENYALANINE DERIVATIVES

TECHNICAL FIELD

The present invention relates to a novel process for synthesizing non-natural amino acids, para- and/or meta-substituted cyanophenylalanine derivatives represented by the following formula (1):

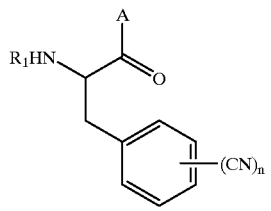

(1)

in which
R₁ represents amino-protecting group,
A represents —OR₂ (wherein, R₂ represents hydrogen, lower-alkyl, cycloalkyl or phenyl) or

wherein, R₃ and R4 independently of one another represent hydrogen, lower-alkyl or cycloalkyl, or together with the nitrogen atom to which they are attached represent heterocyclic group),
n represents an integer of 1 or 2, and the —CN group is located at para or meta position, and their isomers. More specifically, the present invention relates to a process for preparing the compound of formula (1) and its stereoisomer, characterized in that a compound represented by the following formula (2):

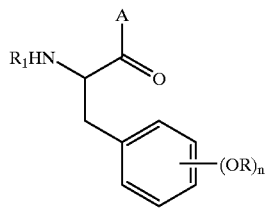

(2)

in which
R represents fluorosulfonyl, trifluoromethanesulfonyl or nonafluorobutanesulfonyl,
R₁, A and n are defined as previously described, and
the —OR group is located at para or meta position, is reacted with a cyanide in the presence of a nickel catalyst.

BACKGROUND ART

The para- and/or meta-substituted cyanophenylalanine derivatives are important intermediate in medicinal chemistry. Particularly, it acts as a very useful intermediate for preparing the thrombin inhibitor LB30057 which has been recently developed by LG Chemical Ltd. as a selective and orally-administered thrombin inhibitor. Therefore, establishment of the effective manufacturing process thereof is very important for preparing LB30057.

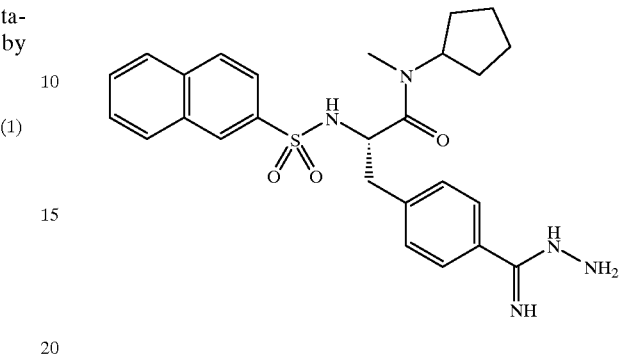

Further, para- and/or meta-substituted cyanophenylalanine derivatives have been used as a key intermediate in the preparation of the existing thrombin inhibitor CRC 220 (*Terahedron*, 1995, 51, 12047) and GPIIb/IIIa receptor antagonist(*J. Med. Chem.* 1996, 39, 1372).

For the synthesis of para- and/or meta-substituted cyanophenylalanine derivatives, catalytic asymmetric hydrogenation (*Terahedron*, 1995, 51, 12047), alkylation of the enolate of glycine derivative(*J. Chem. Soc. Perkin Trans* 1, 1996, 645 and *J. Am. Chem. Soc.* 1997, 119, 656) have been disclosed. These methods, however, have some drawbacks therewith that adeprotection during the synthesis is not easy and large scale production can hardly be achieved thereby.

The present inventors have already developed a process for preparation of said intermediate based on a cyanation reaction using a palladium catalyst as a result of extensive study. Then, we filed a patent application claiming the invention(Korean Patent Application No. 97-41254).

Under such a technical situation, the present inventors have constantly tried to economically and conveniently prepare the useful medicinal intermediate, compound of formula (1) above. During the tries, unexpectedly, we found that such a purpose can be accomplished by reacting the compound of formula (2) with a cyanide in the presence of a nickel catalyst, and then completed the present invention.

DISCLOSURE OF THE INVENTION

Therefore, it is an object of the present invention to provide a process for preparing the compound of formula (1) with a high yield from the phenylalanine derivative of formula (2) in the presence of an inorganic cyanide salt and a nickel catalyst. The process for preparing the compound of formula (1) from the compound of formula (2) is depicted in the following reaction scheme 1.

Reaction Scheme 1

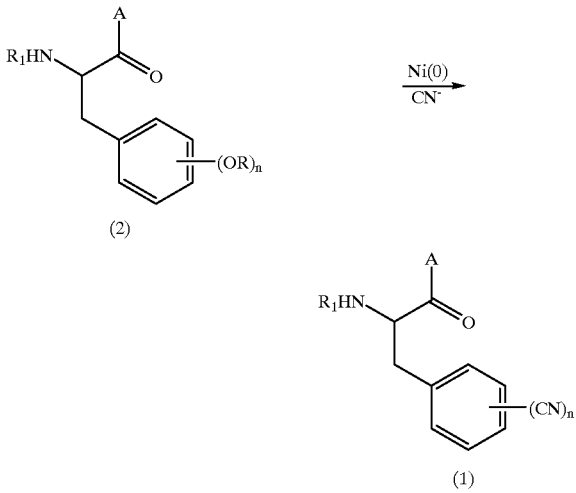

in which
R represents fluorosulfonyl, trifluoromethanesulfonyl or nonafluorobutanesulfonyl,
$R_1$ represents amino-protecting group,
A represents $-OR_2$ (wherein, $R_2$ represents hydrogen, lower-alkyl, cycloalkyl or phenyl) or

(wherein, $R_3$ and $R_4$ independently of one another represent hydrogen, lower-alkyl or cycloalkyl, or together with the nitrogen atom to which they are attached represent heterocyclic group),
n represents an integer of 1 or 2, and
the —CN(or —OR) group is located at para or meta position.

DETAILED DESCRIPIION OF THE INVENTION

The process summarized in the above reaction scheme 1 are more specifically explained as follows.

Through the present specification, the starting and object compounds wherein A is restricted to $-OR_2$ are cited by adding "—A" to the compound number.

In the definitions for the substituents of the compound of fonnula (1), the term "amino-protecting group" means the conventionally used one in the field of organic synthesis, which includes carbonyl groups such as fluorenylmethyloxycarbonyl, phthalyl, t-butoxycarbonyl, benzyloxycarbonyl, etc., or aromatic- or heteroaromatic sulfonyl groups such as toluenesulfonyl, benzenesulfonyl, naphthalenesulfonyl, benzothiazole-2-sulfonyl, 5-methyl-1,3,4-thiadiazole-2-sulfonyl, etc.; the term "lower-alkyl" means a saturated and straight-chain or branched hydrocarbon radical having 1 to 4 carbon atoms, which includes methyl, ethyl, isopropyl, n-butyl, isobutyl and t-butyl; the term "cycloalkyl" means cyclic alkyl having 3 to 8 carbon atoms, which includes cyclopentyl; and the term "heterocyclic group" means 5- or 6-membered saturated or unsaturated ring containing one or two nitrogen atom(s) which may be substituted, the representative example of which is 4-methylsulfonyl-piperazine.

The compound of formula (1) can exist as a pure stereoisomer such as enantiomer of R or S, and therefore, without a specific mention hereinafter, the present invention is understood to include each of these stereoisomers and their mixtures.

The nickel catalyst used in the process according to the present invention is produced by reducing a nickel divalent compound with a reducing agent The nickel divalent compound which can be used for this purpose includes $Ni(PPh_3)_2Cl_2$, $Ni(PPh_3)_2Br_2$, $NiBr_2$, $NiCl_2$, $Ni(acac)_2$, $Ni(OAc)_2$ (wherein, Ph means phenyl, ac or Ac means acetate), etc. These compounds are reduced with zinc, n-BuLi or DIBAL (diisobutylaluminum-chloride) in the reaction solution in the presence of triphenylphosphine or its derivative to produce a Ni compound having 0 valence[Ni(0)] which actually acts as the nickel catalyst in the process according to the present invention. As far as the catalyst thus obtained functions in the desired manner, there are no restriction on the kind of catalyst compound or reducing agent. This reaction has been used for converting trifluoromethanesulfonyl group in a simple benzene compound into cyano group(*Chem. Lett.* 1989, 1957), which, however, has never been applied to the more complicated compounds.

It is preferable to use the catalyst in an amount of 1–20 mol % with respect to the compound of formula (2) since using the excess reagent of more than 20 mol % is uneconomic.

The reducing agent zinc, n-BuLi or DIBAL is suitably used in an amount of 1 equivalent with respect to the nickel divalent compound. However, there is no influence on the reaction when the reducing agent is used in excess. Triphenylphosphine or its derivative which acts as a ligand is used in an amount of 1 to 5 equivalents with respect to the nickel compound because the stabilization of Ni(0) catalyst can be achieved in said range and the reaction can hardly be completed due to the decomposition of the catalyst when the ligand is used in an amount of less than 1 equivalent.

Whatever cyanides generate cyanide ion into the reaction medium can be used in the present invention. Preferably, one or more selected from the group consisting of KCN, NaCN and $Zn(CN)_2$ is used. In the case of KCN and NaCN, the cyanide is preferably used in an amount of 1to 2.5 times molar amount with respect to the compound of formula (2), and in the case of $Zn(CN)_2$, it is preferably used in an amount of 0.5 to 1.5 times molar amount to the compound (2). When the cyanide is used in an amount of more than the respective upper limit, it may react with Ni(0) catalyst to cause the reduction of catalyst activity.

The reaction is carried out at temperatures ranging from 40 to 80° C., and one or more selected from the group consisting of acetonitrile, tetrahydrofuran(THF), dimethylformarnide(DMF), dimethylsulfoxide(DMSO) and N-methylpyrrolidone(NMP) are used as the solvent. The compound of formula (1) may be obtained through the reaction as explained above with a yield of about 80–90%.

While, the compound of formula (2), the starting material in the process of the present invention, may be prepared according to the processes depicted in the following reaction schemes 2 and 3. That is, the compound of formula (2) may be prepared by protecting first the amino group of the cheap starting compound such as D- or L-tyrosine, 3,4-dihydroxyphenylalanine, or ester derivative thereof and then converting the hydroxy group(s) into the corresponding fluorosulfonyloxy, trifluoromethanesulfonyloxy or nonafluorobutanesulfonyloxy group, respectively.

Reaction Scheme 2

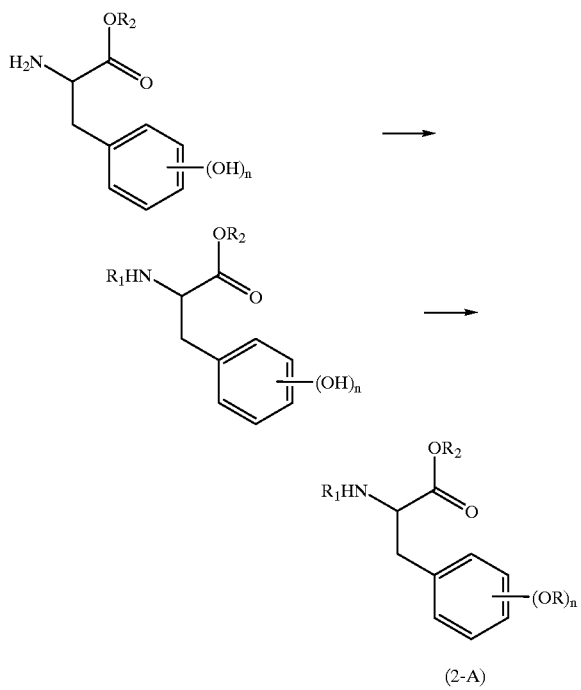

(2-A)

Reaction Scheme 3

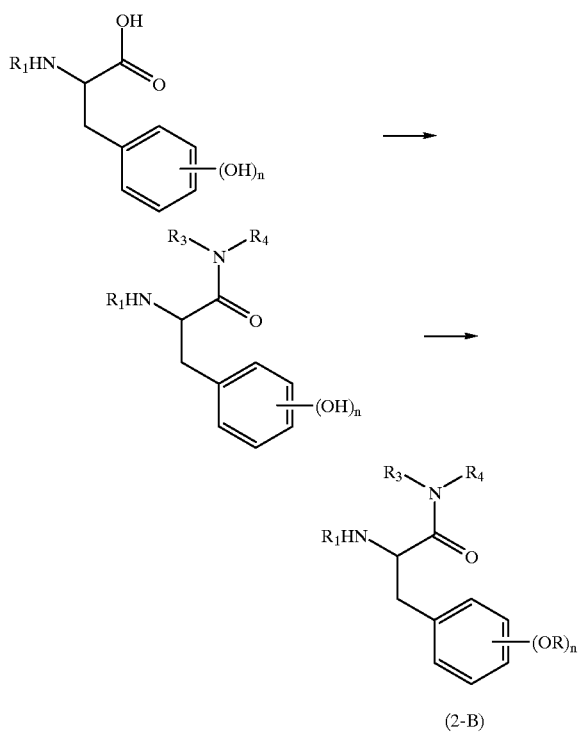

(2-B)

Distinctive feature of the above process represented in reaction scheme 2 is that additional introduction of a separate hydroxy-protecting group is not required in the course of introducing carbonyl or sulfonyl protector into the amino group of the starting compound represented by the following formula (3-A) or its hydrochloride salt:

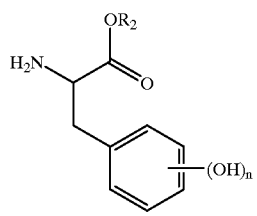

(3-A)

in which, $R_2$ and n are defined as previously described.

In case the product of formula (2) is N-sulfonyl derivative, the starting compound of formula (3-A) or its hydrochloride salt is reacted with trimethylsilylchloride to transiently protect both amino- and hydroxy groups with trimethylsilyl group, the desired sulfonyl protector is selectively introduced into the amino group, and then trimethylsilyl protector is removed from the hydroxy group during the work-up process. In case the product of formula (2) is N-carbonyl derivative, the starting compound of formula (3-A) or its hydrochloride salt is reacted with the corresponding anhydride or chloroformate in the presence of potassium carbonate or sodium carbonate and PEG (polyethyleneglycol) as a phase transition catalyst to selectively introduce the desired carbonyl protector into the amino group.

In the reaction scheme 2, after the introduction of amino-protecting group into the compound (3-A) is completed, the desired functional group is introduced into the hydroxy group to give the compound of formula (2-A). For example, trifluoromethanesulfonyl group may be introduced into the hydroxy group by dissolving the starting compound in a mixture of pyridine and methylene chloride then by reacting with trifluoro- methanesulfonic anhydride. According to the similar process, fluorosulfonyl or nonafluorobutanesulfonyl group may be introduced, respectively.

In the reaction scheme 3, N-protected compound is treated with isobutylchloroformate(i-BuO$_2$CCl) to afford mixed anhydride with concomitant formation of isobutyl-carbonate of the phenylhydroxy group. Thus formed anhydride was quenched with amine(NR$_3$R$_4$) and the carbonate group was cleaved by lithium hydroxide. Then, the hydroxy group thus generated is transformed in the same manner as the reaction scheme 2 to give the compound(2-B).

Typical examples of the compound of formula (2) which can be prepared according to the above processes are as follows.

Methyl-(S)-2-(t-butoxycarbonylamino)-3-(4-trifluoromethanesulfonyloxyphenyl)propionate(2a);

Methyl-(S)-2-(benzyloxycarbonylamino)-3-(4-trifluoromethanesulfonyloxyphenyl)propionate(2b);

Methyl-(S)-2-(fluorenylmethyloxycarbonylamino)-3-(4-trifluoromethanesulfonyloxyphenyl)propionate(2c);

Methyl-(S)-2-(2-naphthalenesulfonylamino)-3-(4-trifluoromethanesulfonyloxyphenyl)propionate(2d);

Methyl-(S)-2-(2-naphthalenesulfonylamino)-3-(4-nonafluorobutanesulfonyloxyphenyl)propionate(2e);

Methyl-(S)-2-(p-toluenesulfonylamino)3-(4-trifluoromethanesulfonyloxyphenyl)propionate(2f);

Methyl-(S)-2-(benzenesulfonylamino)3-(4-trifluoromethanesulfonyloxyphenyl)propionate(2g);

Methyl-(S)-2-(benzothiazole-2-sulfonylamino)-3-(4-trifluoromethanesulfonyloxyphenyl)propionate(2h);

Metbyl-(S)-2-(2-naphthalenesulfonylamino)-3-(4-fluorosulfonyloxyphenyl)propionate(2i);

(S)-N-cyclopentyl-N'-methyl-3-(4-trifluoromethanesulfonyloxyphenyl)-2-(t-butoxycarbonylamino)propionamide(2j);

(S)-N-cyclopentyl-N'-methyl-3-(4-trifluoromethanesulfonyloxyphenyl)-2-[(naphthalen-2-yl)sulfonylamino]propionamide(2k);

(S)-4-[2-(t-butoxycarbonyl-amino)-3-(4-methylsulfonyl-piperazinyl)-3-oxo-propyl]benzenetrifluoromethanesulfonate(2l);

(S)-N-(2-methylpropyl)-3-(4-trifluoromethanesulfonyloxyphenyl)-2-(t-butoxycarbonylamino)propionamide(2m);

(S)-N-butyl-3-(4-trifluoromethanesulfonyloxyphenyl)-2-(t-butoxycarbonylamino)propionamide(2n);

(S)-N-cyclopentyl-3-(4-trifluoromethanesulfonyloxyphenyl)-2-(butoxycarbonylamino)propionamide(2o); and (S)-N-cyclopentyl-N'-methyl-3-(3,4-ditrifluoromethanesulfonyloxyphenyl)-2-(t-butoxycarbonylamino)propionamide(2p).

BEST MODE FOR CARRYING OUT THE INVENTION

The present invention will be more specifically explained in the following preparations and examples. However, it should be understood that they are intended to illustrate the present invention but not in any manner to limit the scope of the present invention.

PREPARATION 1 synthesis of methyl-(S)-2-(t-butoxycarbonylamino)-3-(4-hydroxyphenyl)propionate

Potassium carbonate(10.55 g, 76 mmol) and PEG (M.W.2000, 3 g, 1.5 mmol) were suspended in 120 ml of ethyl acetate. To this mixture was added methyltyrosinate hydrochloride(13.8 g, 59.6 mmol) and the resulting reaction mixture was stirred for about 1.5 hours. t-Butoxycarbonyl anhydride(Boc anhydride)(13 g, 59.6 mmol) was added thereto, the mixture thus obtained was stirred at room temperature for about 20 hours and diluted with 1N HCl solution. The organic layer was separated, and this organic layer was washed with aqueous sodium chloride solution, dried, and concentrated to give 16.2 g(Yield 93%) of the title compound.

$^1$H NMR(CDCl$_3$, 300 MHz) δ 6.9(d, J=7.8 Hz, 2H), 6.71(d, J=7.8 Hz, 2H), 5.29(br.s, 1H), 4.91(br.d, 1H), 4.5(m, 1H), 3.65(s, 3H), 2.95(m, 2H).

The following compounds were prepared according to the similar procedure as Preparation 1 above.

Methyl-(S)-2-(benzyloxycarbonylamino)3-(4hydroxyphenyl)propionate.

Methyl-(S)-2-(fluorenylmethyloxycarbonylamino)-3-(4-hydroxyphenyl)propionate.

PREPARATION 2

Synthesis of methyl-(S)-2-(2-naphthalenesulfonylamino)-3-(4-hydroxyphenyl)propionate Methyltyrosinate(1 g, 4.32 mmol) was suspended in 5 ml of methylene chloride, pyridine(1.4 ml, 17.28 mmol) was added thereto, and the reaction mixture was allowed to stand until the mixture became thoroughly transparent. After the reaction solution became transparent, trimethylsilylchloride (1.1 ml, 8.64 mmol) was slowly added thereto at room temperature. After 1 hour, 2-naphthalenesulfonylchloride (1.08 g, 4.75 mmol) was added and the resulting mixture was stirred for 24 hours. To this mixture was added 3N HCl solution, which was then stirred for about 2 hours. The organic layer was separated, the aqueous layer was extracted with methylene chloride, and the organic layers were combined. The combined organic layer was dried over Na$_2$SO$_4$ and the organic solvent was removed by distillation under reduced pressure. The resulting residue was recrystallized from toluene to give 1.29 g(Yield 79%) of the title compound as a white solid.

$^1$H NMR(CDCl$_3$, 300 MHz) δ 8.33(s, 1H), 7.91(m, 3H), 7.68(m, 3H), 6.90(d, J=8.4 Hz, 2H), 6.62(d, J=8.4 Hz, 2H), 5.18(d, J=9.1 Hz, 1H), 4.92(br.s, 1H), 4.21(dt, J=15, 6.0 Hz, 1H), 3.37(s, 3H), 3.00(dd, J=13.5, 5.7 Hz, 1H), 2.93(dd, J=14.3, 6.5 Hz, 1H).

The following compounds were prepared according to the similar procedure as Preparation 2 above.

Methyl-(S)-2-(p-toluenesulfonylamino)-3-(4-hydroxyphenyl)propionate.

Methyl-(S)-2-(benzenesulfonylamino)-3-(4-hydroxyphenyl)propionate.

Methyl-(S)-2-(benzothiazole-2-sulfonylamino)-3-(4-hydroxyphenyl)propionate.

PREPARATION 3

Synthesis of methyl-(S)-2-(2-naphthalenesulfonylamino)-3-(4-trifluoromethanesulfonyloxyphenyl)propionate(2d)

N-(2naphthalenesulfonyl)methyltyrosinate(1.29 g, 3.35 mmol) was dissolved in pyridine(542 μl, 3.7 mmol) and methylene chloride,(5ml) and the reaction mixture was allowed to stand to a temperature of 0° C. Trifiuoromethane-sulfonyl anhydride(623 μl, 3.7 mmol) was slowly added thereto. After about 3 hours, 1N HCl solution was added and the resulting organic layer was separated. The separated organic layer was dried over Na$_2$SO$_4$, filtered and then the filtrate was distilled under reduced pressure. The residue was recrystallized from 20% aqueous ethanol solution to give 1.48 g(Yield 86%) of the title compound as a white solid.

$^1$H NMR(CDCl$_3$, 300 MHz) δ 8.35(s, 1H), 7.92(m, 3H), 7.68(m, 3H), 7.16(d, J=8.7 Hz, 2H, 7.08(d, J=8.4 Hz, 2H), 5.29(d, J=8.7 Hz, 1H), 4.25(dt, J=8.7, 6.2 Hz, 1H), 3.40(s, 3H), 3.12(dd, J=13.9, 5.7 Hz, 1H), 3.02(dd, J=14.5, 8.1 Hz, 1H).

The following compounds were prepared according to the similar procedure as Preparation 3 above.

Methyl-(S)-2-(t-butoxycarbonylamino)-3-(4-trifluoromethanesulfonyloxyphenyl)propionate(2a).

Methyl-(S)-2-(benzyloxycarbonylamino)-3-(4-trifluoromethanesulfonyloxyphenyl)propionate(2b).

Methyl-(S2-(fluorenylmethyloxycarbonylamino)-3-(4-trifluoromethanesulfonyloxyphenyl)propionate(2c).

Methyl-(S)-2-(p-toluenesulfonylamino)-3-(4-trifluoromethanesulfonyloxyphenyl)propionate(2f).

Methyl-(S)-2-(benzenesulfonylamino)-3-(4-trifluoromethanesulfonyloxyphenyl)propionate(2g).

Methyl-(S)-2-(benzothiazole-2-sulfonylamino)-3-(4-trifluoromethanesulfonyloxyphenyl)propionate(2h).

Further, the same procedure as Preparation 3 was carried out except that nonafluorobutanesulfonylchloride was used instead of trifluoromethanesulfonyl anhydride to give methyl-(S)-2-(2-naphthalenesulfonylamino)-3-(4-nonafluorobutanesulfonyloxyphenyl)propionate(2e), and the same procedure as Preparation 3 was carried out except that fluorosulfonylchloride was used instead of trifluoromethanesulfonyl anhydride to give methyl-(S)-2-(2-naphthalenesulfonylamino)-3-(4-fluorosulfonyloxyphenyl) propionate(2i).

PREPARATION 4

Synthesis of (S)-N-cyclopentyl-N'-methyl-3-(4-trifluoromethanesulfonyloxyphenyl)-2-(t-butoxycarbonylamino)propionamide(2j)

Boc(t-butoxycarbonyl)-tyrosine(70.33 g, 0.25 mol) was dissolved in tetrahydrofuran(450 ml), which was then cooled to −20° C. N-methylmorpholine(101.15 g, 1.0 mol) was added thereto, and isobutylchloroformate(70.0 g, 0.513 mol) was slowly added. Cyclopentylmethylamine hydrochloride(37.30 g, 0.275 mol) was added to the resulting solution, which was then stirred for about 4 hours at room temperature. Tetrahydrofuran was removed and the residue was extracted with 1N hydrochloric acid solution (500 ml) and diethylether(900 ml). The organic layer was dried over anhydrous magnesium sulfate and distilled under reduced pressure. The residue was dissolved in tetrahydrofuran(400 ml) and cooled to −5° C. LiOH.H$_2$O (31.47 g) and water(200 ml) were added thereto and the mixture was stirred for 2 hours. Tetrahydrofuran was removed and the residue was extracted with 1N hydrochloric acid solution(120 ml) and ethylacetate(750 ml). The organic layer was dried over anhydrous magnesium sulfate and distilled under reduced pressure. The residue was dissolved in dichloromethane(470 ml) and pyridine (59.33 g, 0.75 mol), to which was slowly added at −20° C. a solution wherein trifluoromethanesulfonic anhydride(105.80 g, 0.375 mol) was dissolved in dichloromethane(50 ml). The reaction mixture was stirred at the same temperature for 3 hours and extracted with 1N hydrochloric acid solution (300 ml). The organic layer was dried over anhydrous magnesium sulfate and distilled under reduced pressure. The residue was purified by silica gel column chromatography(hexane/ethylacetate=2/1, v/v) to give 450 g(Yield 91%) of the title compound.

PREPARATION 5

Synthesis of (S)-N-cyclopentyl-N'-methyl-3-(4-trifluoromethanesulfonyloxyphenyl)-2-[(naphthalen-2-yl)sulfonylamino]propionamide(2k)

(S)-N-cyclopentyl-N'-methyl-3-(4-trifluoromethanesulfonyloxyphenyl)-2-(t-butoxycarbonylamino)propionamide(1.81 g, 3.66 mmol) prepared in Preparation 4 was dissolved in dichloromethane (20 ml), which was then cooled to 0° C. Trifluoroacetic acid(7.0 ml) was added and the resulting mixture was stirred for 1 hour. Sufficient amount of saturated sodium hydrogen carbonate solution was added thereto to make the mixture weak basic. This mixture was extracted twice with dichloromethane, then the separated organic layer was washed with aqueous sodium chloride solution, dried and concentrated to obtain (S)-N-cyclopentyl-N'-methyl-3-(4-trifluoromethanesulfonyloxyphenyl)-2-aminopropionamide. The resulting compound was dissolved in dichloromethane (17 ml), N-methylmorpholine(654 mg, 6.47 mmol) was added thereto, and the mixture was cooled to 0° C. To this mixture was slowly added the solid (naphthalen-2-yl) sulfonylchloride(0.92 g, 4.05 mmol). After 2 hours, the solution was extracted twice with dichloromethane. The organic layer was combined, washed with aqueous sodium chloride solution, and concentrated under reduced pressure. The concentrate was dissolved in methanol, which was then allowed to stand at room temperature. The resulting solid was filtered to give 1.2 g of the title compound, and the filtrate was concentrated again and crystallized in the same manner to give 0.61 g of the title compound. The total yield of the two steps was 85%.

$^1$H-NMR(CDCl$_3$, ppm)δ :8.32(d, J=8.7 Hz, 1H), 7.88(m, 3H), 7.73(m, 1H), 7.61(m, 2H), 7.21(t, J=7.8 Hz, 2H), 7.11(t, J=7.8 Hz, 2H) 5.97(dd, J=16.3, 9.3 Hz, 1H), 4.51, 4.32, 3.67(q, J=6.9 Hz, m, and quintet, J=8.25, total 2H), 2.96(m, 2H), 2.32, 2.04(s, 3H), 1.45–0.35(m, 8H). MS(FAB, m/e): 585(M$^+$+1).

The following compounds were prepared according to the similar procedure as Preparation 4 or 5 above.

(S)-4-[2-(t-Butoxycarbonyl-amino)-3-(4-methylsulfonyl-piperazinyl)-3-oxo-propyl]benzenetrifluoromethanesulfonate(2l);

(S)-N-(2-methylpropyl)-3-(4-trifluoromethanesulfonyloxyphenyl)-2-(t-butoxycarbonylamino)propionamide(2m);

(S)-N-butyl-3-(4-trifluoromethanesulfonyloxyphenyl)-2-(t-butoxycarbonylamino)propionamide(2n);

(S)-N-cyclopentyl-3(4-trifluoromethanesulfonyloxyphenyl)-2-(t-butoxycarbonylamino)propionamide(2o);

(S)-N-cyclopentyl-N'-methyl-3-(3,4ditrifluoromethanesulfonyloxyphenyl)-2-(t-butoxycarbonylamnino)propionamide(2p).

EXAMPLE 1

Synthesis of methyl-(S)-2-(2-naphthalenesulfonylamino)3-(4-cyanophenyl) propionate Ni(PPh$_3$)$_2$Cl$_2$(15 mol %, 95 mg, 0.145 mmol), PPh$_3$(76 mg, 0.29 mmol), KCN (118 mg, 1.81 mmol), Zn(32 mg, 0.49 mmol) and methyl-(S)-2-(2-naphthalenesulfonylamino)-3-(4-trifluoromethanesulfonyloxyphenyl)propionate(2d)(0.5 g, 0.97 mmol) were dissolved in 2 ml of NMP and the reaction mixture was heated at 55° C. under nitrogen atmosphere for about 2.5 hours. The mixture was cooled to room temperature and 3N HCl solution was added thereto. The mixture was stirred for about 1 hour and the filtrate was distilled under reduced pressure. The residue was separated and purified by column chromatography(silica gel, hexane/ethylacetate=5:1 to 1:1)to give 312 mg(Yield 89%) of the title compound as a white solid.

$^1$H NMR(CDCl$_3$, 300 MHz) δ 8.31(s, 1H), 7.89(m, 3H), 7.67(m, 3H), 7.39(d, J=6.5 Hz, 2H), 7.17(d, J=6.5 Hz, 2H), 5.57(d, J=8.9 Hz, 1H), 4.27(m, 1H), 3.45(s, 3H), 3.15(dd, J=13.8, 4.3 Hz, 1H), 3.00(dd, J=13.4, 6.1 Hz, 1H).

EXAMPLE 2

Synthesis of methyl-(S)-2-(2-naphthalenesulfonylamino)3-(4-cyanophenyl) propionate The title compound was given with a yield of 90% according to the same procedure as Example 1 except that methyl-(S)-2-(2-naphthalenesulfonylamino)-3-(4-nonafluorobutanesulfonyloxyphenyl)propionate(2e) was used as the starting material instead of methyl-(S)-2-(2-naphthalenesulfonylamino)-3-(4-trifluoromethanesulfonyloxyphenyl)propionate(2d).

EXAMPLE 3

Synthesis of methyl-(S)-2-(t-butoxycarbonylamino)-3-(4-cyanophenyl)propionate

The title compound was given with a yield of 90% according to the same procedure as Example 1 except that methyl-(S)-2-(t-butoxycarbonylamino)-3-(4-trifluoromethanesulfonyloxyphenyl)propionate(2a) was used as the starting material instead of methyl-(S)-2-(2-naphthalenesulfonylamino)-3-(4-trifluoromethanesulfonyloxyphenyl)propionate(2d).

$^1$H NMR(CDCl$_3$, 500 MHz) δ 7.57(d, J=7.8 Hz, 2H), 7.24(d, J=7.8 Hz, 2H), 5.03(d, J=6.9 Hz, 1H), 4.59(d, J=6.9 Hz, 1H), 3.73(s, 3H), 3.20–3.05(m, 2H), 1.39(s, 9H).

EXAMPLE 4

Synthesis of methyl-(S)-2-(benzyloxycarbonylamino)-3-(4-cyanophenyl)propionate

The title compound was given with a yield of 88% according to the same procedure as Example 1 except that methyl-(S)-2-(benzyloxycarbonylamino)-3-(4-trifluoromethanesulfonyloxyphenyl)propionate(2b) was used as the starting material instead of methyl-(S)-2-(2-naphthalenesulfonylamino)-3-(4-trifluoromethanesulfonyloxyphenyl)propionate(2d).

$^1$H NMR(CDCl$_3$, 500 MHz) δ 7.7–7.2(m, 9H), 5.1(s, 2H), 4.95(d, J=6.9 Hz, 1H), 4.59(d, J=6.9 Hz, 1H), 3.78(s, 3H), 3.20–3.05(m, 2H).

EXAMPLE 5

Synthesis of methyl-(S)-2-(fluorenylmethyloxycarbonylamino)-3-(4-cyanophenyl)propionate The title compound was given with a yield of 92% according to the same procedure as Example 1 except that methyl-(S)-2-(fluorenylmethyloxycarbonylamino)-3-(4-trifluoromethanesulfonyloxyphenyl)propionate(2c) was used as the starting material instead of methyl-(S)-2-(2-naphthalenesulfonylamino)-3-(4-trifluoromethanesulfonyloxyphenyl)propionate(2d).

$^1$H NMR(CDCl$_3$, 500 MHz) δ 7.9–7.1(m, 17H), 4.95(d, J=6.9 Hz, 1H), 4.59(m, 3H), 4.20(t, 1H), 3.78(s, 3H), 3.28–3.1(m, 2H).

EXAMPLE 6

Synthesis of methyl-(S)-2-(p-toluenesulfonylamino)-3-(-4-cyanophenyl)propionate

The title compound was given with a yield of 87% according to the same procedure as Example 1 except that methyl-(S)-2-(p-toluenesulfonylamino)-3-(4-trifluoromethanesulfonyloxyphenyl)propionate(2f) was used as the starting material instead of methyl-(S)-2-(2-naphthalenesulfonylamino)-3-(4-trifluoromethanesulfonyloxyphenyl)propionate(2d).

$^1$H NMR(CDCl$_3$, 300 MHz) δ 7.8(d, J=7.5 Hz, 2H), 7.4(d, J=7.5 Hz, 2H), 7.30(d, J=6.5 Hz, 2H), 7.05(d, J=6.5 Hz, 2H), 5.30(d, J=9.1 Hz, 1H), 4.27(m, 1H), 3.45(s, 3H), 3.10(dd, J=13.8, 4.3 Hz, 1H), 3.05(dd, J=13.4, 6.1 Hz, 1H), 2.7(s, 3H).

EXAMPLE 7

Synthesis of methyl-(S)-2-(benzenesulfonylamino)-3-(4-cyanophenyl)propionate

The title compound was given with a yield of 89% according to the same procedure as Example 1 except that methyl-(S)-2-(benzenesulfonylamino)-3-(4-trifluoromethanesulfonyloxyphenyl)propionate(2g) was used as the starting material instead of methyl-(S)-2-(2-naphthalenesulfonylamino)-3-(4-trifluoromethanesulfonyloxyphenyl)propionate(2d).

$^1$H NMR(CDCl$_3$, 300 MHz) δ 7.8–7.30(m, 7H), 7.05(d, J=6.5 Hz, 2H), 5.26(d, J=9.1 Hz, 1H), 4.19(m, 1H), 3.38(s, 3H), 3.19(dd, J=13.8, 4.3 Hz, 1H), 3.10(dd, J=13.4, 6.1 Hz, 1H).

EXAMPLE 8

Synthesis of (S)-N-cyclopentyl-N'-methyl-3-(4-cyanophenyl)2-(t-butoxycarbonylamino) propionamide To a mixture of (S)-N-cyclopentyl-N'-methyl-3-(4-trifluoromethanesulfonyloxyphenyl)-2-(t-butoxycarbonylamino)propionamide(2j)(1 g,2.02 mmol) prepared in Preparation 4, triphenylphosphine(106 mg, 0.404 mmol), potassium cyanide(197 mg, 3.03 mmol), zinc (132 mg, 2.02 mmol) and Ni(PPh$_3$)$_2$Cl$_2$(65.4 mg, 0.10 mmol) was added N-methylpyrrolidone(NMP)(2ml) at room temperature under nitrogen atmosphere, and the whole mixture was stirred. After stirring for about 5 minutes, the initial green color of the reaction mixture was changed to dark red-brown. This mixture was heated at 75° C. for about 3 hours and then cooled to room temperature. To the mixture was added 3N hydrochloric acid solution(10 ml), the resulting mixture was stirred for about 30 minutes and then ethylacetate(15 ml was added thereto. After the organic layer was separated from the mixture, the separated organic layer was washed with saturated aqueous sodium chloride solution(10 ml), dried over anhydrous sodium sulfate, and then filtered. The filtrate was concentrated under reduced pressure and the residue was purified by silica gel column chromatography(hexane/ethylacetate=7/3, v/v) to give 632 mg(1.72 mmol, Yield 85%) of the title compound.

$^1$H NMR(CDCl$_3$, ppm) δ 7.61(m, 2H), 7.32(m, 2H), 5.48, 5.01, 4.86, 4.12(3m, 3H), 3.02(m, 2H), 2.75, 2.62(2s, 3H), 1.90–1.20(m, 17H); MS(FAB, m/e): 371 (M$^+$+1).

EXAMPLE 9

Synthesis of (S)-4-[2-(t-butoxycarbonyl-amino)-3-(4-methylsulfonyl-piperazinyl)-3-oxo-propyl] benzonitrile The title compound was given with a yield of 90% according to the same procedure as Example 8 except that (S)-4-[2-(t-butoxycarbonyl-amino)-3-(4-methylsulfonyl-piperazinyl)-3-oxo-propyl] benzenetrifluoromethanesulfonate (2l) was used as the starting material instead of (S)-N-cyclopentyl-N'-methyl-3-(4-trifluoromethanesulfonyloxyphenyl)-2-(t-butoxycarbonylamino)propionamide(2j).

$^1$H NMR(CDCl$_3$, ppm) δ 7.70–7.30(m, 4H), 5.30(m, 1H), 4.81(m, 1H), 3.90–2.81(m, 8H), 2.71(s, 3H), 1.50(s, 9H); MS(FAB, m/e): 437(M$^+$+1).

EXAMPLE 10

Synthesis of (S)-N-(2-methylpropyl)-3-(4cyanophenyl)-2-(t-butoxycarbonylamino)propionamide The title compound was given with a yield of 89% according to the same procedure as Example 8 except that (S)-N-(2-methylpropyl)-3-(4-trifluoromethanesulfonyloxyphenyl)-2-(t-butoxycarbonylamino)propionamide(2m) was used as the starting material instead of (S)-N-cyclopentyl-N'-methyl-3-(4-trifluoromethanesulfonyloxyphenyl)-2-(t-butoxycarbonylamino)propionamide(2j).

$^1$H NMR(CDCl$_3$, ppm) δ 7.60(m, 2H), 7.33(m, 2H), 6.03(m, 1H), 5.07(m, 1H), 4.30(m, 1H), 3.20–3.00(m, 4H), 1.68(m, 1H), 1.50(s, 9H), 0.82(s, 6H); MS(FAB, m/e): 318(M$^+$+1).

EXAMPLE 11

Synthesis of (S)-N-butyl-3-(4-cyanophenyl)-2-(t-butoxycarbonylamino)propionamide The title compound was given with a yield of 88% according to the same procedure as Example 8 except that (S)-N-butyl-3-(4-trifluoromethanesulfonyloxyphenyl)-2-(t-butoxycarbonylamino)propionamide(2n) was used as the starting material instead of (S)-N-cyclopentyl-N'-methyl-3-(4-trifluoromethanesulfonyloxyphenyl)-2-(t-butoxycarbonylamino)propionamide(2j).

$^1$H NMR(CDCl$_3$, ppm) δ 7.63(m, 2H), 7.49(m, 2H), 6.03(m, 1H), 5.18(m, 1H), 4.38(m, 1H), 3.28–3.13(m, 4H), 1.51(s, 9H), 1,52–1.28(m, 4H), 0.98(m, 3H); MS(FAB, m/e): 318(M$^+$+1).

EXAMPLE 12

Synthesis of (S)-N-cyclopentyl-3-(4-cyanophenyl)-2-(t-butoxy-carbonylamino)propionamide The title compound was given with a yield of 90% according to the same procedure as Example 8 except that (S)-N-cyclopentyl-3-(4-trifluoromethanesulfonyloxyphenyl)-2-(t-butoxycarbonylamino) propionamide(2o) was used as the staring material instead of (S)-N-cyclopentyl-N'-methyl-3-(4-trifluoromethanesulfonyloxyphenyl)-2-(t-butoxycarbonylamino)propionamide(2j).

$^1$H-NMR(CDCl$_3$, ppm) δ 7.60(m, 2H), 7.32(m, 2H), 5.79(m, 1H), 5.08(m, 1H), 4.24(m, 1H), 4.12(m, 1H), 3.12(m, 2H), 1.90–1.21(m, 8H), 1.5(s, 9H); MS(FAB, m/e): 330(M$^+$+1).

EXAMPLE 13

Synthesis of (S)-N-cyclopentyl-N'-methyl-3-(3,4dicyanophenyl)-2-(t-butoxycarbonylamino)propionamide The title compound was given with a yield of 89% according to the same procedure as Example 8 except that (S)-N-cyclopentyl-N'-methyl-3-(3,4-ditrifluoromethanesulfonyloxyphenyl)-2-(t-butoxycarbonylamino)propionamide(2p) was used as the starting material instead of (S)-N-cyclopentyl-N'-methyl-3-(4-trifluoromethanesulfonyloxyphenyl)-2-(t-butoxycarbonylamino)propionamide(2j).

$^1$H-NMR(DMSO-d$_6$, ppm) δ 8.10(m, 2H), 7.85(m, 1H), 4.90, 4.55–4.79, 4.28 (3m, 3H), 1.80–1.10(m, 17H); MS(FAB, m/e): 397(M$^+$+1).

EXAMPLE 14

Synthesis of (S)-N-cyclopentyl-N'-methyl-3-(4-cyanophenyl)-2-[(naphthalen-2-yl)sulfonylaminol]propionamide The title compound was given with a yield of 90% according to the same procedure as Example 8 except that (S)-N-cyclopentyl-N'-methyl-3-(4-trifluoromethanesulfonyloxyphenyl)-2-[(naphthalen-2-yl)sulfonylamino]propionamide(2k) was used as the starting material instead of (S)-N-cyclopentyl-N'-methyl-3-(4-trifluoromethanesulfonyloxyphenyl)-2-(t-butoxycarbonylamino)propionamide(2j).

$^1$H-NMR(CDCl$_3$, ppm) δ 8.28(d, J=10.1 Hz, 1H), 7.88(d, J=8.7 Hz, 3H), 7.69(m, 1H), 7.62(m, 2H), 7.48(dd, J=7.48, 2.8 Hz, 2H), 7.23(m, 2H), 5.96(dd, J=17.5, 9.2 Hz, 1H), 4.52, 4.34, and 3.78(m, m, quintet, 2H), 2.95(m, 2H), 2.35, 2.22(s, 3H), 1.58–0.38(m, 8H); MS(FAB, m/e): 462(M$^+$+1).

According to the process of the present invention, the uset. medicinal intermediate of para- and/or meta-substituted cyanophenylalanine derivative can be obtained with a high yield by reacting the cheap starting material with cyanide in the presence of a nickel catalyst.

What is claimed is:

1. A process for preparing a compound represented by the following formula 1:

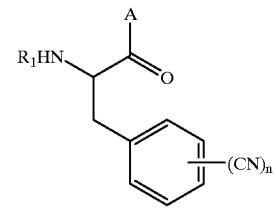

in which

R$_1$ represents amino-protecting group,

A represents i) —OR$_2$ wherein R$_2$ represents hydrogen, lower alkyl, cycloalkyl or phenyl, or ii)

wherein R$_3$ and R$_4$ independently of one another represent hydrogen, lower alkyl or together with the nitrogen atom to which they are attached represent a heteroalicyclic group, n represents an integer of 1 or 2, the —CN or —OR group is located at para or meta position, or its steroisomer, characterized in that a compound represented by the following formula 2:

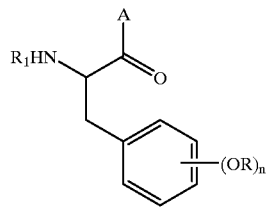

in which

R₁, A and n are as defined above, and

R represents fluorosulfonyl, trifluoromethanesulfonyl or nonafluorobutanesulphonyl, is reacted with a cyanide in the presence of a nickel catalyst.

2. The process of claim 1, wherein the nickel catalyst is obtained by reducing a nickel divalent compound by a reducing agent.

3. The process of claim 2, wherein the nickel divalent compound is one or more selected from a group consisting of $Ni(PPh_3)_2Cl_2$, $Ni(PPh_3)_2Br_2$, $NiBr_2$, $NiCl_2$, $Ni(acac)_2$ and $Ni(OAc)_2$.

4. The process of claim 3, wherein the nickel divalent compound is used in an amount of 1 to 20 mol % with respect to the compound of formula (2).

5. The process of claim 2, wherein the reducing agent is one or more selected from a group consisting of zinc, n-BuLi and diusobutylaluminumchloride(DIBAL).

6. The process of claim 5, wherein the reducing agent is used in an amount of 1 equivalent or more with respect to the nickel divalent compound.

7. The process of claim 1, wherein the cyanide is one or more selected from a group consisting of KCN, NaCN and $Zn(CN)_2$.

8. The process of claim 7, wherein KCN or NaCN is used in an amount of 1 to 2.5 times molar amount and $Zn(CN)_2$ is used in an amount of 0.5 to 1.5 times molar amount, with respect to the compound of formula (2).

9. The process of claim 1, wherein triphenylphosphine or its derivative is further used in an amount of 1 to 5 equivalents with respect to the nickel catalyst.

10. The process of claim 1, wherein the compound of formula 2 has a structure of the following formula 2-A:

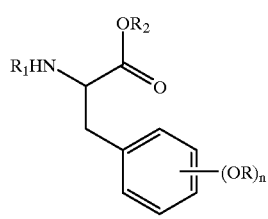

in which R, R₁, R₂ and n are as defined in claim 1, is obtained by the steps comprising reacting a compound represented by the following formula 3-A:

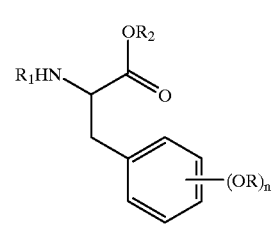

in which R₂ and n are defined as claim 1, or its hydrochloride salt with trimethnylsilylchloride, then by selectively introducing a sulfonyl protector to the amino group.

11. The process of claim 1, wherein the compound of formula 2 has a structure of the following formula 2-A:

2-A

[same structure as 2-A above]

in which R, R₁, R₂ and n are defined in claim 1, is obtained by the steps comprising reacting a compound represented by the following formula 3-A:

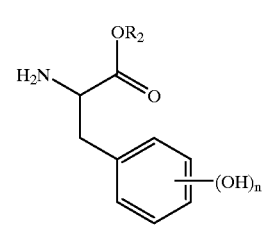

in which R₂ and n are defined as claim 1, or its hydrochloride salt with the corresponding anhydride or chloroformate in the presence of potassium carbonate or sodium carbonate and polyethyleneglycol as a phase transition catalyst to selectively introduce a carbonyl protector to the amine group.

12. The process of claim 12 wherein the compound of formula 2 is prepared from D-tyrosine, L-tyrosine, 3,4-dihydroxyphenylalanine, or ester thereof.

13. The process of claim 12 wherein a hydroxy group of D-tyrosine, L-tyrosine, 3,4-dihydroxyphenylalanine, or ester thereof, is converted into corresponding fluorosulfonyloxy, trifluoromethanesulfonyloxy or nonafluorobutanesulfonyloxy group.

14. The process of claim 1 wherein the compound of formula (2) is selected from the group consisting of:

Methyl-(S)-(t-butoxycarbonylamino)-3-(4-trifluoromethanesulfonyloxyphenyl)propionate;

Methyl-(S)-2-(benzyloxycarbonylamino)-3-(4-trifluoromethanesulfonyloxyphenyl)propionate;

Methyl-(S)-2-(fluorenylmethyloxycarbonylamino)-3-(4-trifluoromethanesulfonyloxyphenyl)propionate;

Methyl-(S)-2-(2-naphthalenesulfonylamino)-3-(4-trifluoromethanesulfonyloxyphenyl)propionate;

Methyl-(S)-2-(2-naphthalenbesulfonylamino)-3-(4-nonafluorobutanesulfonyloxyphenyl)propionate;

Methyl-(S)-2-(p-toluenesulfonylamino)-3-(4-trifluoromethanesulfonyloxyphenyl)propionate;

Methyl-(S)-2-(benzenesulfonylamino)-3-(4-trifluoromethanesulfonyloxyphenyl)propionate;

Methyl-(S)-2-(benzothiazole-2-sulfonylamino)-3-(4-trifuoromethanesulfonyloxyphenyl)propionate;

Methyl-(S)-2-(2-naphthalene sulfonylamino)-3(4-fluorosulfonyloxyphenyl)propionate;

(S)-N-cyclopentyl-N'-methyl-3-(4-trifluoromethanesulfonyloxyphenyl)-2-(t-butoxycarbonylamnino)propionamide;

(S)-N-cyclopentyl-N'-methyl-3-(4-trifluoromethanesulfonyloxyphenyl)-2-[(naphthalene-2-yl)sulfonylamnino]propionamide;

(S)4-[2-(t-butoxycarbonyl-amino)-3-(4-methylsulfonyl-piperazinyl)-3-oxopropyl]benzenetrifluoromethanesulfonate;

(S)-N-(2-methylpropyl)-3-(4-trifluoromethanesulfonyloxyphenyl)-2-(t-butoxycarbonylamino)propionamide;

(S)-N-butyl-3-(4-trifluoromethanesulfonyloxyphenyl)-2-(t-butoxycarbonylamino)propionamide;

(S)-N-cyclopentyl-3-(4-trifluoromethanesulfonyloxyphenyl)-2-(t-butoxycarbonylamino)propionamide; and (S)-N-cyclopentyl-N'-methyl-3-(3,4-ditrifluoromethanesulfonyloxyphenyl)-2-(t-butoxycarbonylamino)propionamide.

15. A process for preparing a compound represented by the following formula 1 and being produced in an enantiomeric excess of a steroisomer of R configuration or S configuration:

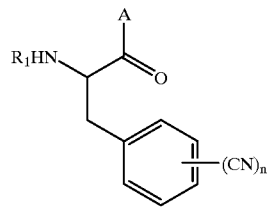

1 in which $R_1$ represents amino-protecting group,

A represents i) —$OR_2$ wherein $R_2$ represents hydrogen, lower alkyl cycloalkyl or phenyl, or ii)

wherein $R_3$ and $R_4$ independently of one another represent hydrogen, lower alkyl or together with the nitrogen atom to which they are attached represent a heteroalicyclic group, n represents an integer of 1 or 2, the —CN or —OR group is located at para or meta position, or its steroisomer, characterized in that a compound represented by the following formula 2:

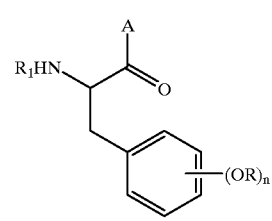

2 in which $R_1$, A and n are as defined above, and

R represents fluorosulfonyl, trifluoromethanesulfonyl or nonafluorobutanesulphonyl, is reacted with a cyanide in the presence of a nickel catalyst.

16. The process of claim 15 wherein the compound of formula (1) is produced in an enantiomeric excess of a stereoisomer of R configuration.

17. The process of claim 15 wherein the compound of formula (1) is produced in an enantiomeric excess of a stereoisomer of S configuration.

* * * * *